United States Patent [19]
Jung et al.

[11] Patent Number: 6,124,357
[45] Date of Patent: Sep. 26, 2000

[54] IODINATED FATTY ACID ESTERS IODINATED FATTY ACIDS AND DERIVATIVES THEREOF PRODUCED BY IODOHYDRINATION USING ALKYLSILYLATED DERIVATIVES AND ALKALINE IODIDES AND THE PHARMACOLOGICAL ACTIVITIES THEREOF

[76] Inventors: Louis Jung, 205 route d'Oberhausbergen, 67200 Strasbourg; Yves Ingenbleek, 24 boulevard d'Anvers, 67000 Strasbourg, both of France

[21] Appl. No.: 08/981,931

[22] PCT Filed: Jul. 10, 1996

[86] PCT No.: PCT/FR96/01075

§ 371 Date: Jan. 12, 1998

§ 102(e) Date: Jan. 12, 1998

[87] PCT Pub. No.: WO97/03038

PCT Pub. Date: Jan. 30, 1997

[30] Foreign Application Priority Data

Jul. 11, 1995 [FR] France .................................... 95 08582

[51] Int. Cl.$^7$ .................................................... A61K 31/22
[52] U.S. Cl. .......................... 514/546; 514/552; 514/557; 514/558; 514/743; 514/825; 554/225; 554/226; 554/227; 554/159; 424/9.4
[58] Field of Search ................................ 554/159, 225, 554/226, 227; 424/9.4; 514/552, 557, 588, 743, 825

[56] References Cited

FOREIGN PATENT DOCUMENTS

| 0315323 | 10/1986 | Germany . |
|---|---|---|
| 35 13 323 | 10/1986 | Germany . |
| 3513323 | 10/1986 | Germany . |
| 53-119817 | 10/1978 | Japan . |

OTHER PUBLICATIONS

Chem Abstr., Asano et al, abstrast of EP–300749, #112:62622, 1989.

Chem. Abstr., Iguchi et al, abstract of JP–60/214731, #104:75067, 1985.

*Primary Examiner*—Deborah D. Carr
*Attorney, Agent, or Firm*—Young & Thompson

[57] ABSTRACT

Iodinated fatty acid esters, iodinated fatty acids and fluid pharmaceutical-grade stable derivatives thereof are produced by iodohydrination in an organic medium using alkylsilylated derivatives, such as trimethylsilyl chloride or trimethylchlorosilane, that react with an alkaline iodide such as sodium iodide, whereafter hydroiodic acid is formed in situ by exposure to water and the hydroiodic acid is reacted with fatty acid esters and particularly rapeseed oil fatty acid methyl esters that may be used as a biofuel for gasoline engines to provide a low-cost product, and are used therapeutically, in particular for treating goitre linked to iodine deficiency.

18 Claims, No Drawings

IODINATED FATTY ACID ESTERS IODINATED FATTY ACIDS AND DERIVATIVES THEREOF PRODUCED BY IODOHYDRINATION USING ALKYLSILYLATED DERIVATIVES AND ALKALINE IODIDES AND THE PHARMACOLOGICAL ACTIVITIES THEREOF

This application is a 371 of PCT/FR96/01075 filed Jul. 10, 1996.

BACKGROUND OF THE INVENTION

The invention relates to iodinated fatty acid esters and iodinated fatty acids and derivatives thereof obtained by iodohydrination involving the introduction of alkylsilylated derivatives with alkaline iodides used in the treatment of endemic goitre and pharmaceutical compositions containing them. They can also be used as contrast compounds in radiology and as a vehicle for chemiembolisation.

Endemic goitre is a deficiency disease which constitutes one of the most serious problems of public health confronting the World Health Organisation (WHO). According to official WHO records, a thousand million individuals, that is 20% of the population of the world, is affected by an iodine deficiency, mainly in developing countries (Hetzel B. S., Potter B. J. and Dulberg E. M. The iodine deficiency disorders: nature, pathogenesis and epidemiology. World Rev. Nutr. Diet. 62: 59–119 (1990)). Almost all of these countries are affected with very variable degrees of prevalence. In the most severely affected regions, it is possible to count up to 80% of subjects suffering from thyroid dysfunction: this is manifested by the appearance of unattractive hypertrophy of the glands which can develop into secondary hypothyroidism with neurological problems. Adolescent girls and women of child-bearing age are most widely exposed and can give birth to a high proportion of up to 10% of newborn babies suffering from a particular form of irreversible mental disability known as endemic cretinism and considered as the most threatening medical and social complication.

It is universally accepted that an iodine deficiency in the diet is the primary and predominant cause of this nutritional scourge.

The geological nature and the geographical environment therefore appear to be the main factors determining this situation although certain dietary factors are incriminated as aggravating secondary causes. The appropriate treatment therefore involves supplementing deficient populations with additions of iodine covering physiological requirements.

Theoretically, this objective is easy to achieve. However, experience over recent decades has shown that the traditional vehicles for iodine supplementation (drinking water, table salt, bread -flour) encounter major problems in diffusion associated with the transportation, storage and consumption conditions, in (sub) tropical regions. In fact, iodine is administered in the form of sodium or potassium iodide or iodate liberating halogen in a non-storable form in adipose tissues. It is therefore necessary to take the iodinated vehicle daily for years. The nutritional benefits are irregular and slow to obtain, and this form of supplementation does not allow the urgent problems encountered in regions of high prevalence to be overcome rapidly.

There is also an iodinated oil having long-lasting effect known as Lipiodol® (Société Guerbet) which, when administered in a single annual oral or parenteral dose, has demonstrated anti-goitre preventive and therapeutic effects. This iodinated oil, designed as a contrast product in radiology, is produced from rare and relatively expensive poppy-seed oil (Somnifer papaverum). Although the high tolerance and curative properties of Lipiodol® have been known for a long time, this product has not become established as a tool for massive eradication owing to the relatively high cost with respect to the huge requirements of the Third World.

SUMMARY OF THE INVENTION

Our invention aims to overcome this handicap: a new iodinated drug is proposed which is formed from iodinated fatty acid esters or iodinated fatty acids and derivatives thereof which are of pharmaceutical purity, stable, free of toxic contaminants, totally iodinated, have no double bonds, are obtained by action of an alkylsilylated reagent and an alkaline iodide on fatty acid esters or fatty acids and have therapeutic properties.

For example, it is possible to produce low cost iodinated fatty acid esters from iodinated fatty acid methyl esters obtained by original synthesis from rapeseed oil (Brassica campestris) used as biological fuel in car engines having a very low cost price, and this allows mass campaigns to be envisaged. The new product allows better bio-availability and an extended therapeutic effect because the iodine is fixed on the three fatty acids (oleic acid n-9, linoleic acid n-6 and α-linolenic acid n-3), of which the last two are essential and which are precursors of the three main fatty acids metabolic pathways. To avoid the risks of viral contamination through blood (hepatitis B and C, HIV), exclusively oral administration of our iodinated product is proposed. Several methods have already been described for the transformation of unsaturated fatty acids or of unsaturated fatty acid esters in iodinated saturated derivatives.

DESCRIPTION OF PREFERRED EMBODIMENTS

Oleic acid can be subjected to hydrobromation followed by nucleophilic substitution via potassium iodide after action of hydrobromic acid (J. F. Lane and H. W. Heine: On cyclic Intermediates in Substitution Reactions. I The Alkaline Hydrolysis of Some Aliphatic Bromoacids. J. Am. Chem. Soc. 1951, 73, 1348–1350). Olive oil cooled to the region of the setting point is saturated directly with hydriodic acid. Other fatty acids have been envisaged. (A. Guerbet, A. Gibaud, G. Tilly, R. Joussot, V. Loth and M. Guerbet; Monoiodostéarate d'éthyle. Préparation et caractères analytiques. Ann. pharm. fr., 1965, 23, No. 11, 663–671). Direct iodination with hydroiodic acid is also carried out using dehydrating substances such as polyphosphoric acids, phosphorus pentoxide (W. Kuhn, H. Hartner, F. Schindler, I. Sandner and K. Hering; German patent P 35 13 322.6/C 07 C 69/62, 1985). Hydroiodination can also be carried out with iodine in the presence of alumina generating hydroiodic acid (L. J. Stewart, D. Gray, R. M. Pagni and G. W. Kabalka; A Convenient Method for the addition of HI to unsaturated hydrocarbons using $I_2$ on $Al_2O_3$, Tetrahedron Lett, 1987, Vol. 28, No. 39, 4497–4498). Hydroiodination has also been carried out using the boron-N, N-diethylamine complex involving boron triiodide. (Ch. Kishan Reddy and M. Periasamy; A new, simple procedure for the generation and addition of HI to alkenes and alkynes using $BI_3$: N, N-diethylaniline complex and acetic acid. Tetrahedron Lett., 1990, Vol. 31, No. 13, 1919–1920). Hydroiodination with potassium iodide in orthophosphoric acid can also be envisaged (Organic. Synthesis, Vol. 9, 66).

The document JP-A-53119817 is also known, which discloses the synthesis of glyceryl tri-(2-iodohexadecanoate) in two stages.

In the first stage, 2-bromopalmitoyl chloride is reacted with glycerine in a water-free benzene/pyridine solvent to obtain 36% of glyceryl tri- (2-bromohexadecanoate) after purification.

This is then reacted with NaI in acetone to yield 74% of glyceryl tri-(2-iodohexadecanoate) after treatment with $Na_2S_2O_3$, purification, drying, etc.

As specified, among others, in German patent No. C 07 C 69/62/P 3513 323.8 dated 13.4.1985 and belonging to W. Kuhn et al, the methods for the preparation of odinated compounds lead to products containing toxic impurities and products which are unstable in air and light during the preparation and storage thereof. Our method of preparation leads, in particular, to a product having various constituents and no double bond which is a source of instability, in particular in the presence of oxidation derivatives and free radicals.

Iodinated fatty acid esters prepared by iodohydrination involving alkysilylated derivatives and an alkaline iodide forming the subject of the invention exhibit the form of a pharmaceutically pure, stable, light yellow, fluid, oily liquid having a relatively low cost price. The fatty acid esters used for the preparation of iodinated derivatives involving an alkylsilylated compound and an alkaline iodide can be, for example, fatty acid triglycerides originating from vegetable oils of the rapeseed oil, poppy-seed oil, soya oil, safflower oil, groundnut oil, grapeseed oil, sunflower oil, linseed oil, corn oil, olive oil, sesame oil, wheatgerm oil, coconut oil and palm oil type and from oils of animal origin.

The fatty acid esters used can also be mixtures of fatty acid methyl esters or ethyl esters originating form vegetable oils of the rapeseed oil, poppy-seed oil, soya oil, safflower oil, groundnut oil, grapeseed oil, sunflower oil, linseed oil, corn oil, olive oil, sesame oil, wheatgerm oil, coconut oil and palm oil type and oils of animal origin.

It is of particular interest for large-scale production of drugs to use a raw material for the synthesis of fatty acid methyl esters originating from rapeseed oil used as biological fuel for car engines having a low cost price.

Fatty acids of the oleic acid, linoleic acid, α-linolenic acid, erucic acid, arachidonic acid and ricinoleic acid type can also be used as raw materials.

The process for obtaining iodinated fatty acid esters or iodinated fatty acids involves reacting an alkaline iodide with an alkylsilylated halide in an organic medium giving rise, in the presence of water, to hydroiodic acid in situ reacting either with the fatty acid ester or esters or with the fatty acids.

To obtain iodinated fatty acid esters or iodinated fatty acids, for example, sodium iodide is reacted with trimethylsilyl chloride or trimethylchlorosilane in acetonitrile followed by the action of water and an addition either of unsaturated fatty acid esters or of unsaturated fatty acids.

The iodohydrination of fatty acid esters can be carried out according to the following reaction:

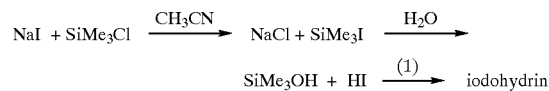

(1) fatty acid esters or fatty acids

The mode of operation, for example, for unsaturated fatty acid esters is as follows: 89.25 ml of trimethylchlorosilane (or trimethylsilyl chloride) are added to a solution of 107.1 g of sodium iodide in 550 ml of acetonitrile in a nitrogen atmosphere and at 0C. 6.65 ml of water are added dropwise after total addition of the trimethylchlorosilane. A solution of 70 g of unsaturated fatty acid methyl or ethyl esters of rapeseed oil is then added. After 24 hours of reaction with stirring, the reaction is then stopped with 700 ml of water. The mixture is extracted using ether. The organic phase is washed several times with a 10% solution of sodium thiosulphate then several times with water. It is dried over anhydrous sodium sulphate and the ether is evaporated at 90° C. over 16 mm Hg (2133 PA) in order to eliminate the remains of siliceous ether. The residue is brown. The iodinated fatty acid esters dissolved in ether are then bleached over coal then filtered over alumina to eliminate the peroxides. The ether is evaporated and the traces of solvent are eliminated using a vane pump. The mixture of iodinated fatty acid esters obtained is golden yellow and has good fluidity. This mixture can be identified by 1H NMR and 13C NMR spectrometry. This method of synthesis of iodinated fatty acid esters was carried out over greater quantities. Other water-immiscible solvents can be used. The insolubility of sodium chloride in acetonitrile allows the total displacement of the reaction toward the formation of trimethylsilyl iodide. This reaction is exothermic and allows the generation of hydrlodic acid and hydroxylated trimethylsilyl.

The secondary product $SiMe_3OH$ is eliminated after the iodohydrination reaction by simple evaporation under reduced pressure and washing in water. The iodohydrination reaction is visually followed by the bleaching (decolonization) of the solution. The sodium thiosulphate allows the elimination of the iodine present in oxidized from. In the final product, no NMR signal of the proton and carbon 13 NMR signal corresponds to an ethylene system. On the other hand, no degradation product appears in NMR of the proton.

Characteristics of rapeseed oil iodinated fatty acid esters:

Nuclear magnetic resonance of the proton ($NMR^1H$) and of the carbon 13 ($NMR^{13}C$). An $NMR^1H$ spectrum of the iodinated fatty acid esters of rapeseed oil allows the disappearance of the ethylene protons to be checked by comparison with the spectrum of the non-iodinated fatty acid esters of rapeseed oil. Furthermore, this allows the absence of traces of solvent diethylether and of silica ether to be checked. Moreover, an $NMR^{13}C$ spectrum allows the disappearance of the carbons carrying the non-saturations to be checked.

The $NMR^1H$ spectra obtained for several productions of iodinated fatty acid ethyl esters of rapeseed oil are identical. No spectrum reveals the presence of diethylether or silica ether.

$NMR^1H$ spectrum of iodinated fatty acid ethyl esters [$NMR^1H$ ($CDCl_3$) over 200 MHz]: 0.89 ppm (3H, m, $CH_3$), 1.20–2.00 ppm (m, $CH_2$ of the chains and CH$_3$CH$_2$O), 2.3 ppm (2H,t,CH$_2$—COOEt), 4.2 ppm (m, CHI, CH$_2$—OOC)

NMR$^{13}$C spectrum of iodinated fatty acid ethyl esters [NR$^3$C (CDCl$_3$) over 200 MHz]: 14 ppm (CH$_3$ at the chain end and CH$_3$CH$_2$O), 28–29 ppm (CHI) 22–24, 30–31, 34 ppm (CH$_2$ of the chains), 39–41 ppm (CH$_2$—CHI), 60 ppm (CH$_2$—O), 173 ppm (COO).

The infrared absorption spectrum (NaCl) has the following characteristic bands: γ (C=O ester) at 1740 cm$^{-1}$; γ (saturated CH) at 2850 cm$^{-1}$, γ(saturated CH) at 2950 cm$^{-1}$ NMR$^1$H spectrum of iodinated fatty acid methyl esters [(NMR$^1$H (CDCl$_3$) over 200 MHz]: 0.89 ppm (3H, m, CH$_3$), 1.25–1.30 ppm (m, CH$_2$ of the chains, 1.60–1.80 ppm (m, CH$_2$) 2.3 ppm (2H,t,CH$_2$—COO), 3.66 ppm (3H,s, CH$_3$—OOC), 4.12 ppm (m, CHI).

NMR$^{13}$C spectrum of iodinated fatty acid methyl esters [NMR$^{13}$C (CDCl$_3$) over 200 MHz]: 14 ppm (CH$_3$ at the chain end), 28–29 ppm (CHI), 22–24, 31–34 ppm (CH$_2$ of the chains), 38–41 ppm (CH2—CHI), 51 ppm (CH$_3$—O), 173 ppm (COO).

Stability: as iodinated products are generally unstable substances, it is necessary to be assured of the stability of the iodinated fatty acid esters and/or of the iodinated fatty acids. Stability is investigated by NMR$^1$H, by thin film chromatography and by quantitative analysis of the iodine bound to the fatty acid esters or on the fatty acids.

NMR$^1$H spectra were produced after 2 months, 3 months and 8 months of storage at a temperature of 20–22° C., sheltered from the light. All three are identical to the spectrum obtained during production. Thin film chromatography (silica gel plate GF 254—moving phase: diethylether/hexane 1:20—examination in ultraviolet light at 254 nm and after atomization of a 10% m/V solution of phosphomolybdenic acid R in alcohol and heating of the plate to 120° C. for 5 min) gives observed spots of which the intensity and position are identical with regard to the freshly prepared product and those stored for 8 months.

Stability of iodinated fatty acid esters of rapeseed oil after use in therapy on the field: the mixture of iodinated fatty acid esters of rapeseed oil was used in investigations into patients in Africa in a region of endemic goitre. During these investigations, the iodinated esters were subjected to extreme conditions (transportation, exposure to light for several hours and at temperatures of about 45° C.). After two weeks of investigations, the iodinated fatty acid esters were analyzed: the NMR$^1$H spectrum was found to be identical to that of a freshly synthesized oil and thin layer chromatography yields spots identical to those of freshly synthesized iodinated fatty acid esters and does not reveal a degradation product.

Test of tolerance on rats: before administering the mixture of iodinated fatty acid esters of rapeseed oil to goitrous subjects, the tolerance of the mixture of iodinated esters was tested on adult male rats weighing about 300 g. Each test group consists of 5 rats which each receive an oral administration of 0.5 ml of mixture of iodinated fatty acid esters of rapeseed oil. The rats were kept under observation. After one week, the behaviour and general state of the rats in each test group are normal and identical to those of the control group. The iodinated products prepared by the above-described method are used as generally administered drugs, for example as anti-goitre drugs in the pure state or in combination with appropriate excipients in the form of a drinkable or ingestable liquid, capsules or ampoules for example. These iodinated products can also be used as generally or topically administered drugs, for example as contrast products or as antiinflammatory agents in rheumatoid therapy. These products can be used as drugs which are administered in a general or local vascular manner in the treatment of certain cancers by chemiembolisation involving administering an anti-cancer drug emulsioned in iodinated fatty acid esters which act as carries for tumoral lipophilic cells.

What is claimed is:

1. Process for obtaining at least one iodinated fatty acid or at least one iodinated fatty acid ester or iodinated derivatives thereof which have pharmaceutical purity, are stable and free from toxic impurities, characterized in that it involves reacting an alkaline iodide with an alkylsilylated reagent in an organic medium giving rise in the presence of water to hydroiodic acid in situ reacting with the fatty acid(s), the fatty acid ester(s) or derivatives thereof in such a way that all the double bonds initially present in the fatty acid(s) or fatty acid ester(s) or derivatives thereof are saturated in iodine in a proportion of one molecule of hydroiodic acid per double bond.

2. Process according to claim 1, characterized in that the alkaline iodide is sodium iodide.

3. Process according to claim 1, characterized in that the alkylsilylated reagent is an alkylsilylated halide.

4. Process according to claim 3, characterized in that the alkylsilylated halide is trimethylsilyl chloride or trimethylchlorosilane.

5. Process according to claim 1, characterized in that the organic medium contains acetonitrile.

6. Process according to claim 1, characterized in that the fatty acid ester(s) consist(s) of fatty acid triglyceride(s) originating from vegetable oil(s) selected from the group formed by rapeseed oil, poppy-seed oil, soya-oil, safflower oil, groundnut oil, grapeseed oil, sunflower oil, linseed oil, corn oil, olive oil, sesame oil, wheatgerm oil, coconut oil, palm oil and oils of animal origin.

7. Process according to claim 1, characterized in that the fatty acid ester(s) consist(s) of fatty acid methyl ester(s) originating from vegetable oil(s) selected from the group formed by rapeseed oil, poppy-seed oil, soya-oil, safflower oil, groundnut oil, grapeseed oil, sunflower oil, linseed oil, corn oil, olive oil, sesame oil, wheatgerm oil, coconut oil, palm oil and oils of animal origin.

8. Process according to claim 7, characterized in that the fatty acid ester(s) consist(s) of fatty acid methyl ester(s) originating from rapeseed oil, used as low cost price biological fuel for car engines.

9. Process according to claim 1, characterized in that the fatty acid ester(s) consist(s) of fatty acid ethyl ester(s) originating from vegetable oil(s) selected from the group formed by rapeseed oil, poppy-seed oil, soya-oil, safflower oil, groundnut oil, grapeseed oil, sunflower oil, linseed oil, corn oil, olive oil, sesame oil, wheatgerm oil, coconut oil, palm oil and oils of animal origin.

10. Process according to claim 1, characterized in that the fatty acid(s) is/are selected from the group formed by oleic acid, linoleic acid, α-linolenic acid, erucic acid, arachidonic acid and ricinoleic acid.

11. A drug comprising one of an iodinated fatty acid, iodinated fatty acid ester and iodinated derivatives thereof, all double bonds initially present in the one of the iodinated fatty acid, iodinated fatty acid ester, and iodinated derivative thereof being saturated in iodine in a proportion of one molecule of hydroiodic acid per double bond, the drug being stable and free of toxic impurities and of a stabilizing reactant.

12. A method for the preventive and/or therapeutic treatment of goitre comprising administering to a patient in need of said treatment the drug of claim 11 in a pure state or in combination with excipients in drinkable or ingestable form.

13. A method for anti-inflammatory treatment in rheumatoid therapy comprising administering to a patient in need of said treatment the drug of claim 11 by general or topical methods.

14. A method for the treatment of cancers comprising administering to a patient in need of said treatment the drug of claim 11 by chemiembolization.

15. The method of claim 14, wherein the iodinated fatty acid, iodinated fatty acid ester or iodinated derivative thereof is a carrier for an anti-cancer drug emulsified in said iodinated fatty acid, iodinated fatty acid ester or derivatives thereof, for treating tumoral lipophilic cells.

16. A contrast product comprising the drug of claim 11.

17. The drug of claim 11 comprising the iodinated fatty acid ester that is a fatty acid triglyceride selected from the group of vegetable oils consisting of rapeseed oil, groundnut oil, and olive oil.

18. The drug of claim 11 comprising the iodinated fatty acid ester that is a fatty acid ethyl or methyl ester selected from the group of oils consisting of rapeseed oil, groundnut oil, and olive oil.

* * * * *